United States Patent [19]

Leonardi et al.

[11] Patent Number: 4,806,534

[45] Date of Patent: Feb. 21, 1989

[54] THERAPEUTICALLY ACTIVE FLAVONYL-1,4-DIHYDROPHYRIDINES

[75] Inventors: Amedeo Leonardi; Renzo Pennini; Pietro Cazzulani; Dante Nardi, all of Milan, Italy

[73] Assignee: Recordati S.A., Chemical & Pharmaceutical Company, Chiasso, Switzerland

[21] Appl. No.: 921,397

[22] Filed: Oct. 22, 1986

[30] Foreign Application Priority Data

Oct. 22, 1985 [IT] Italy .............................. 22578 A/85

[51] Int. Cl.$^4$ .................. A61K 31/445; C07D 407/02
[52] U.S. Cl. .................. 514/233.5; 514/253; 514/318; 514/316; 514/337; 514/232.5; 546/269; 546/187; 546/193; 544/131; 544/365
[58] Field of Search ...................... 546/269, 187, 193; 544/131, 365; 514/337, 316, 318, 236, 253

[56] References Cited

U.S. PATENT DOCUMENTS 2,921,070  1/1960  da Re ................................. 549/403
4,532,248  7/1985  Franckowiak et al. ............ 514/358

FOREIGN PATENT DOCUMENTS 3311005  9/1984  Fed. Rep. of Germany .

OTHER PUBLICATIONS

Thomas et al. J. of Cardiovasular Phar. 6: 1170-1176 1984.
Schramm et al., Nature vol. 303. 9. Jun. 1983.
Bossert et al. Angew. Chem. Int. Ed. Engl. 20, 762-769 (1981).
"Novel dihydropyridines with positive inotropic action through activation of Ca$^{2+}$ Channels," M. Schramm et al, Letters to Nature vol. 303, Jun. 9, 1983.
"Drug treatment of the overactive detrusor", K. E. Andersson et al, Acta pharmacol, et toxicol. 1980, 46 Suppl. I, (7-11).
"Effect of Calcium Channel Blockers on Urinary Tract Smooth Muscle", Karl Brik Andersson et al, Acta Pharmacol Toxicol 58 (supple. II), 1986.
"Anticholinergic and calcium antagonistic effects of terrodiline in rabbit urinary bladder", S. Husted, et al, Acta Pharmacol. et Toxicol 1980.46 (Suppl. I.) (20-30).

Primary Examiner—Jane T. Fan
Attorney, Agent, or Firm—Burns, Doane, Swecker & Mathis

[57] ABSTRACT

The novel flavonyl-1,4-dihydropyridines having the general formula (I):

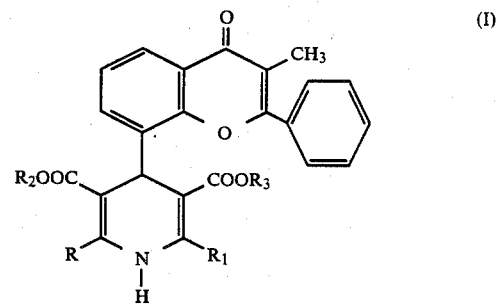

are therapeutically effective calcium antagonists and smooth muscle relaxant.

61 Claims, No Drawings

THERAPEUTICALLY ACTIVE FLAVONYL-1,4-DIHYDROPHYRIDINES

BACKGROUND OF THE INVENTION

1. Field of the Invention

The present invention relates to novel flavone compounds which are useful calcium antagonists, as well as smooth muscle relaxants (in particular, on the bladder), to processes for their preparation, and to pharmaceutical compositions comprised thereof.

2. Description of the Prior Art

It is known to this art, from U.S. Pat. No. 2,921,070, that certain ester of 3-methylflavon-8-carboxylic acid exhibit excellent spasmolytic activity.

Moreover, it too is known to this art that a variety of compounds having a 1,4-dihydropyridine basic nucleus, and substituted in the 3,5-positions by ester functions, display calcium-antagonistic activity.

In German Pat. No. 3,311,005, for example, 1,4-dihydropyridine derivatives are described which have chromone or thiochromone substituents, but all are monoesters, bearing only hydrogen, or nitro, cyano, halogen, alkyl, fluoroalkyl or hydroxycarbonyl substituents at the 5-position of the dihydropyridine nucleus. These particular compounds are disclosed as being useful cardiotonic agents, to improve heart contractility, and as anti-hypotonic agents, to lower blood sugar, for detumescing mucous membranes, and to influence salt and liquid balance.

SUMMARY OF THE INVENTION

A major object of the present invention is the provision of a novel class of 1,4-dihydropyridine/3-methylflavone compounds, which novel compounds are important calcium antagonists and smooth muscle relaxants (especially on the bladder).

Briefly, the novel compounds provided by this invention have the general formula (I):

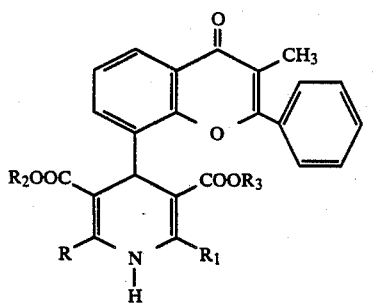

wherein R and $R_1$, which may be identical or different, are each an alkyl radical having from 1 to 4 carbon atoms, a hydroxyalkyl radical having 1 to 4 carbon atoms, or a formylalkyl or cyanoalkyl radical, and $R_2$ and $R_3$, which also may be identical or different, are each a straight or branched chain alkyl radical having from 1 to 6 carbon atoms, a straight or branched chain alkenyl radical having from 2 to 6 carbon atoms, an alkynyl radical having from 2 to 6 carbon atoms, a cycloalkyl radical having from 5 to 7 carbon atoms, an aralkyl radical, a phenyl radical, a cyanoalkyl radical, a haloalkyl radical, a mono- or polyhydroxyalkyl radical, a monoalkyloxyalkyl radical, an alkylthioalkyl radical, an alkylsulfonylalkyl radical, a monoacyloxyalkyl radical, an acylalkyl radical, or an $R_4R_5N$-alkyl straight or branched chain radical having from 2 to 6 carbon atoms, in which $R_4$ and $RHD 5$, which may be identical or different, are each hydrogen, an alkyl radical, a cycloalkyl radical, an aralkyl radical, a phenyl radical, a 3,3-diphenylpropyl radical, or, alternatively, together with the nitrogen atom from which they depend, a saturated or unsaturated heterocyclic ring having from 4 to 7 ring members, and optionally containing one or more other heteroatoms, such as O, N or S, or an $NR_6$ radical, in which $R_6$ is an alkyl radical. This invention also features the optical isomers and diasteroisomers of the compounds (I), as well as the pharmaceutically acceptable salts thereof. Advantageously, the various alkyl, alkoxy and acyl moieties of the aforesaid combination radicals are lower alkyl, lower alkoxy and lower acyl moieties having up to about 8 carbon atoms.

Preferably at least one of R or R, comprises an alkyl radical having 1 to 4 carbon atoms, a hydroxyalkyl radical having 1 to 4 atoms, a formyl(lower alkyl) radical, or a cyano (lower alkyl) radical. Further preferred embodiments are where at least one of $R_2$ or $R_3$ comprise a straight or branched chain alkyl radical having from 1 to 6 carbon atoms, a straight or branched chain alkenyl radical having 2 to 6 carbon atoms, a $R_2$ or $R_3$ alkynyl radical having 2 to 6 carbon atoms, a cycloalkyl radical having 5 to 7 carbon atoms, an ar(lower alkyl) radical, a phenyl radical, a cyano(lower alkyl) radical, a halo(lower alkyl) radical, a mono-or polyhydroxy(lower alkyl) radical, a monohydroxy(lower alkyl) radical, a lower alkylthio(lower alkyl) radical, a lower alkylsulfonyl(lower alkyl)radical, a mono(lower acyl)oxy(lower alkyl) radical, a lower acyl(lower alkyl) radical, or an $R_4R_5$ N-alkyl radical, the alkyl moiety of which being straight or branched chain and having from 2 to 6 carbon atoms, and in which $R_4$ and $R_5$, which may be identical or different, are each hydrogen, or a lower alkyl, lower cycloalkyl, lower aralkyl, phenyl or 3,3-diphenylpropyl radical, with the proviso that $R_4$ and $R_5$ may together form, with the nitrogen atom from which they depend, a saturated or unsaturated heterocycle having from 4 to 7 ring members, and optionally containing one or more other O, S or N heteroatoms, or a group $NR_6$, in which $R_6$ is a lower alkyl radical.

DETAILED DESCRIPTION OF THE PREFERRED EMBODIMENTS OF THE INVENTION

More particularly according to the present invention, the subject compounds having the formula (I) are conveniently prepared, either by:

(a) reacting an aldehyde having the formula (II):

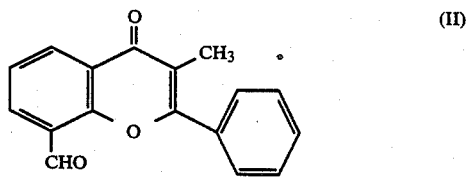

with a ketoester having the formula (III):

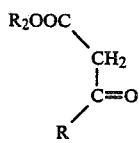

(III)

and with an enamine having the formula (IV):

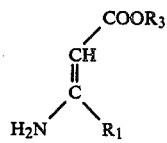

(IV)

wherein R, $R_1$, $R_2$ and $R_3$ are as defined above, and in which R, $R_1$ may facilely be transformed by known procedures into, e.g., formylalkyl, hydroxyalkyl, or cyanoalkyl radicals, or, alternatively:

(b) by treating an aldehyde (II) with a compound having the formula (V):

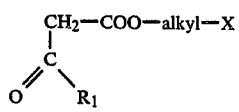

(V)

wherein $R_1$ is defined as in (a) and X is a halogen atom, and reacting the arylidene derivative thus formed with an enamine having the formula (VI):

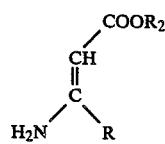

(VI)

wherein R and $R_2$ are as defined above, and optionally adding an amine of the formula $R_4R_5NH$, wherein $R_4$ and $R_5$ are as above defined, or alternatively:

(c) reacting an aldehyde (II) with a ketoester having the formula (III) and then adding to the resulting arylidene derivative an enamine having the formula (VII):

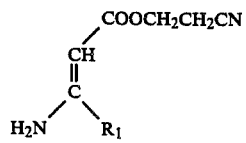

(VII)

wherein R, $R_1$ and $R_2$ are as above defined, or defined under (a), further hydrolyzing the 1,4-dihydropyridinic cyanoethylester thus formed to give the acid having the formula (VIII):

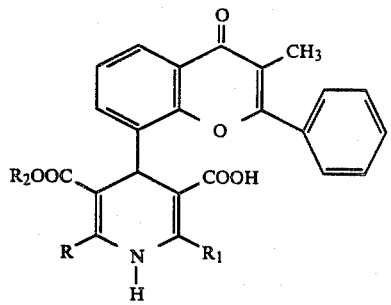

(VIII)

and then esterifying (VIII), following known procedures, with a compound of the formula $R_3OH$ or $R_3X$, in which X is a halogen atom and $R_3$ is as defined above.

The reaction of scheme (a) is typically carried out in a lower alcohol, at the reflux temperature of the alcohol used, for a period of 2-5 hours. Ethanol is the preferred alcohol. After cooling and standing, the precipitated material is isolated in usual manner and optionally purified by recrystallization.

The reaction between (II) and (V) in the scheme (b) is typically carried out in a chlorinated hydrocarbon, preferably chloroform, whereas the further addition of (VI) is in a lower alcohol, preferably isopropanol. The optional further reaction with the amine of the formula $R_4R_5NH$ is carried out in dimethylformamide, under stirring, at a temperature of about 100° C.

The reaction of scheme (c) is carried out, in the first step, in chloroform; the subsequent addition of the enamine (VII) is in alcohol (isopropanol), the hydrolysis of the cyanoethylester is in dimethoxyethane and, finally, the esterification of the acid thus obtained is in dimethylformamide.

The transformation of R or $R_1$ into a formylalkyl radical is carried out by cyclization of a compound of the formula (VII) or (III), in which R or $R_1$ is geminal dialkoxyalkyl, and then by hydrolysis, with hydrochloric acid in acetone, of the resultant 1,4-dihydropyridinic ring of the formula (I), having in R or $R_1$ the aforesaid dimethoxyalkyl group.

The formalkyl radical can be reduced to the corresponding hydroxyalkyl radical using sodium borohydride in ethanol, or, alternatively, can be converted into the corresponding cyanoalkyl group, by means of hydroxylamine and acetic anhydride.

For more details on the aforesaid reaction schemes for the preparation of the compound (I), see the working examples to follow.

All of the intermediates of the formulae (III)–(VIII) are known compounds, or can easily be prepared following known procedures.

The salts according to the invention may be prepared from the basic esters obtained as described above according to conventional methods, such as addition of an acid to the free base dissolved in a suitable solvent. Suitable acids include hydrogen halides, phosphoric acid, nitric acid, alkylsulfonic acids, arylsulfonic acids, monofunctional and bifunctional carboxylic acids, hydroxycarboxylic acids and 1,5-naphthalenedisulfonic acid, and isolation and purification may be effected conventionally.

The novel compounds having the general formula (I) display marked calcium-antagonistic activity and/or a relaxing activity on smooth musculature (in particular, on the musculature of the bladder) and, moreover, are characterized by low toxicity.

Thus, the present invention also features pharmaceutical compositions containing, as active constituent thereof, a compound of the formula (I), together with the usual carriers, supports and diluents. The formulations can be in the form of tablets, capsules, pills, granulates, syrups, emulsions, suspensions and solutions, and are prepared in usual manner by mixing the active substances with solvents and/or carriers, optionally adding emulsifying agents and/or dispersants; whenever water is used as the diluent, organic solvents can also be used as adjuvants. Administration thereof is in usual manner, preferably per oral or by parenteral route. In the case of oral administration, the pharmaceutical forms suitable for this purpose can also contain additives, as well as various supplementary materials, such as starch, gelatin or the like. In the case of liquid forms, compatible colorants, or taste-correcting materials can be added. For parenteral administration, solutions of the active agent are added with the usual liquid excipients well known to those skilled in this art.

The novel compounds according to the present invention inhibit the receptor binding of $^3$H-nitrendipine, thus demonstrating calcium-antagonistic activity. They augment the bladder capacity and reduce the micturition pressure and the contractility of the detrusor muscle in addition to having very low toxicity. From tests performed on rats, it has been shown that in order to elicit optimal activity in relaxing the smooth musculature of the bladder, it is generally advisable to administer the subject compounds per oral route.

The $LD_{50}$ of the novel compounds of the invention was determined in mice, both i.p. and p.o., following the method described by C. S. Weil, *Biometrics*, 8, 249 (1952). Exemplary results are reported in Table 1.

TABLE 1

| Active compound | $LD_{50}$ mg/kg (mice) | |
|---|---|---|
| | i.p. | p.o. |
| i | 889 | >3000 |
| iii | >1000 | >3000 |
| iv | 222 | >3000 |
| v | 959 | >3000 |
| vi | >1000 | >3000 |
| viii | >1000 | >3000 |
| xii | 597 | >3000 |

The activity on calcium-antagonistic binding site was detected "in vitro" by displacement of $^3$H-nitrendipine, according to the method of Bolger et al, *J. Pharm. Exp. Ther.*, 225, 291 (1983).

For the binding assays, rat brain membranes were used, the reaction mixture (2 ml) was incubated for 60 minutes at 25° C. together with $^3$H-nitrendipine (0.45 nM) and various concentrations of the tested compound. $IC_{50}$'s values were determined from inhibition curves derived from the binding of the $^3$H-nitrendipine to its respective binding site in the presence of the antagonist compound, and calculated nonlinearly.

Exemplary results are reported in Table 2.

TABLE 2

| Activity on calcium-antagonistic binding site (rat) | |
|---|---|
| Active compound | $IC_{50}$ (nM) |
| i | $5.55 \times 10^{-9}$ |
| iii | $8.81 \times 10^{-9}$ |

TABLE 2-continued

| Activity on calcium-antagonistic binding site (rat) | |
|---|---|
| Active compound | $IC_{50}$ (nM) |
| iv | $3.03 \times 10^{-7}$ |
| v | $8.36 \times 10^{-9}$ |
| vi | $1.30 \times 10^{-7}$ |
| viii | $3.06 \times 10^{-9}$ |
| x | $1.35 \times 10^{-8}$ |
| xi | $5.45 \times 10^{-8}$ |
| xii | $3.19 \times 10^{-8}$ |
| xiv | $1.46 \times 10^{-8}$ |
| xvi | $3.96 \times 10^{-9}$ |
| xviii | $1.66 \times 10^{-8}$ |
| xx | $4.91 \times 10^{-8}$ |

By $IC_{50}$ is intended the concentration of a compound which reduces specific binding of $^3$H-nitrendipine to 50% of its maximal value.

The activity on the urodynamic parameters was detected by cystometric recordings, carried out in conscious rats, according to the method of Pietra et al, *IRCS Medicinal Science*, in press (1986), similar to that described by Sjogren, *Acta Pharmacol. Toxicol.*, 39, 177 (1976). The intravesical pressure was recorded during a continuous infusion of saline (37° C.) into the urinary bladder at the constant rate of 0.15 ml/min. The bladder volume capacity (BVC), and micturition pressure (MP), were recorded before and after administration of the compounds per oral route. The perfusion started 60 minutes after administration of the compound.

Exemplary results obtained are reported in Table 3, wherein BVC is the bladder volume capacity, and MP is the micturition pressure.

TABLE 3

| Cystometric recordings (rat) | | | |
|---|---|---|---|
| Active compound | Dose (mg/kg p.o.) | % Change BVC | % Change MP |
| i | 10 | +18 | −14 |
| | 30 | +21 | −19 |
| iii | 30 | +15 | −1 |
| v | 10 | +19 | −16 |
| | 30 | +22 | −23 |
| vi | 30 | +31 | −1 |

In order to further illustrate the present invention and the advantages thereof, the following specific examples are given, it being understood that same are intended only as illustrative and in nowise limitative.

EXAMPLE 1

Preparation of 3-methyl-8-formylflavone (II)

A mixture of 59.74 g of 3-methyl-8-chlorocarbonylflavone (obtained from 3-methylflavon-8-carboxylic acid and thionyl chloride, white crystals, m.p. 156°–156.5° C.), 200 ml of xylene, 6 g of 5% palladium on barium sulfate and 0.4 ml of quinoline-S, maintained under stirring and under hydrogen flow, was heated for 6–7 hours at 85°–90° C. Upon completion of the reaction, the mixture was cooled, diluted with chloroform (20 ml), filtered, the solvent was evaporated under vacuum, and 260 ml of 20% sodium hydrogensulfite (W/V) and 600 ml of water were added to the residue. The mixture thus obtained was heated at reflux for 2 hours and then filtered while hot. The cooled filtrate was extracted several times with ethyl ether (4×200 ml), concentrated hydrogen chloride added and then heated to 95°–100° C. for 2 hours. After cooling, the solid thus formed was filtered and washed with water. The product (II) was obtained in a global yield equal to 78% of theoretical (41.46 g) and could be used as such in further syntheses. After recrystallization from methyl-tert-butyl-ether, it melted at 124°–126° C.

Procedural scheme (a)

Dimethyl 2,6-dimethyl-4-(3-methylflavon-8-yl)-1,4-dihydropyridine-3,5-dicarboxylate (i)

A mixture of 7.94 g of 3-methyl-8-formylflavone (obtained as described above), 4.1 g of methyl acetoacetate, 4.14 g of methyl 3-aminocrotonate and 22.5 ml of ethanol was heated at reflux in the dark and under stirring for 4 hours. After cooling to room temperature, the mixture was maintained overnight at 5° C., then the insoluble fraction thus obtained was filtered, washed with ice-cooled ethanol (3×5 ml) and crystallized, first from ethanol and then from methanol until constant m.p. (245°–249° C.). By concentration of the liquors of crystallization, an additional 5.33 g of product were obtained which, combined with the 4.05 g previously obtained, increased the global yield of the title compound to 9.38 g.

Bis-2,N-piperidinoethyl 2,6-dimethyl-4-(3-methylflavon-8-yl)-1,4-dihydropyridine-3,5-dicarboxylate (ii)

This compound, melting at 210°–216° C. after crystallization from acetonitrile/ethyl acetate, was prepared following the procedure described above, but using, instead of methyl acetoacetate and methyl 3-aminocrotonate, 2,N-piperidinoethyl acetoacetate and 2,N-piperidinoethyl 3-aminocrotonate (prepared following usual procedures).

EXAMPLE 2

Procedural scheme (b)

Step 1

Preparation of beta-chloroethyl 2-(3-methylflavon-8-methyliden)acetoacetate

A mixture of 52.8 g of (II), 32.84 g of beta-chloroethylacetoacetate and 400 ml of toluene was saturated at 0°/+5° C. with gaseous hydrochloric acid. The mixture was permitted to stand at room temperaure for 24–48 hours, then nitrogen was bubbled therethrough to expel the acid and the solvent was evaporated. The residue was washed first with hot ethyl ether (2×100 ml) and then with cold ethyl ether (1×100 ml) to obtain 70 g of the title compound as the sole stereoisomer, melting at 130°–131° C.

STEP 2

Isopropyl beta-chloroethyl 2,6-dimethyl-4-(3-methylflavon-8-yl)-1,4-dihydropyridine-3,5-dicarboxylate (iii)

A mixture of 51.35 g of the aforedescribed acetoacetate and 7.15 ml of isopropyl 3-aminocrotonate in 94 ml of isopropanol, maintained under stirring and protected from light, was heated to 80° C. for 2 hours. After cooling, the solid precipitae thus formed was separated by filtration and washed with isopropanol (3×30 ml) to obtain 53 g of the title compound that was used as such for further reactions.

A sample, crystallized from acetone for elemental analysis, melted at 235°–237° C.

Step 3

Isopropyl 2,N-piperidinoethyl 2,6-dimethyl-4-(3-methylflavon-8-yl)-1,4-dihydropyridine-3,5-dicarboxylate (iv)

A mixture of the above compound and 2.13 g of piperidine in 20 ml of anhydrous dimethylformamide, maintained under stirring, under a nitrogen atmosphere and in the dark was heated at 100° C. for 3 hours, then cooled and poured into 100 ml of ice-cold water. The solid precipitate thus formed was filtered, washed with water and, after drying, chromatographed on a silica-gel column (ethyl acetate/methanol (9:1) as eluent). After evaporation of the solvent, the title compound was obtained as residue. The yield was 2.92 g, after crystallization from ethyl acetate, m.p. 205°–206° C.

Following the procedure of Step 3 of this Example, but using N-methylbenzylamine instead of piperidine, isopropyl 2-(N-benzyl-N-methylamino)ethyl 2,6-dimethyl-4-(3-methylflavon-8-yl)-1,4-dihydropyridine-3,5-dicarboxylate (v) was obtained, melting at 170°–172° C. (ethanol).

In the same manner, but employing N-methyl-3,3-diphenylpropylamine instead of piperidine, isopropyl 2-(N-(3,3-diphenylpropyl)-N-methylamino)ethyl 2,6-dimethyl-4-(3-methylflavon-8-yl)-1,4-dihydropyridine-3,5-dicarboxylate was obtained (vi), melting at 151°–153° C. (ethanol).

EXAMPLE 3

Procedural scheme (c)

Step 1

Preparation of methyl 2-(3-methylflavon-8-methyliden)acetoacetate

Following the procedure described in Step 1 of Example 2 for the preparation of beta-chloroethyl 2-(3-methylflavon-8-methyliden)acetoacetate, but starting from a solution comprising 39.6 g of (II) and 17.4 g of methylacetate in 150 ml of chloroform, the title compound was prepared (38.55 g).

STEP 2

Methyl 2-cyanoethyl 2,6-dimethyl-4-(3-methylflavon-8-yl)-1,4-dihydropyridine-3,5-dicarboxylate (vii)

Following the procedure described in Step 2 of Example 2, but using a mixture of 36.2 g of the above acetoacetate and 15.42 g of 2-cyanoethyl 3-aminocrotonate in 60 ml of isopropanol, 42 g of the title compound were prepared and used for the subsequent reaction without further purification. A sample, crystallized from methylenechloride/ethyl ether for elemental analysis, melted at 190°–192° C.

Step 3

Preparation of 2,6-dimethyl-4-(3-methylflavon-8-yl)-1,4-dihydropyridine-3,5-dicarboxylic acid monomethylester hydrate To a solution of 25 g of the 2-cyanoethyl derivative above described, in 250 ml of dimethoxyethane maintained at 20°–25° C. under stirring and in the dark were added dropwise, first, 150 ml of water and then 100 ml of 1N sodium hydroxide. The mixture was maintained at the same temperature for about 2 hours, then was extracted with chloroform (2×6.5 ml) and then with ethyl ether (1×6.5 ml). The aqueous phase was added to ice and acidified to pH 2-3 with hydrochloric acid, and the precipitate thus formed was filtered, washed, dried and crystallized from methanol to give 11.67 g of the title compound, melting at 159°-160° C.

Step 4

Methyl ethyl 2,6-dimethyl-4-(3-methylflavon-8-yl)-1,4-dihydropyridine-3,5-dicarboxylate (viii)

A mixture of 9.26 g of the acid prepared as described above, 4.6 g of dicyclohexylcarbodiimide, 0.24 g of 4-N,N-dimethylaminopyridine and 9.2 ml of ethanol in 40 ml of anhydrous dimethylformamide, maintained under stirring in the dark and under a nitrogen atmosphere, was heated at 80° C. for 24 hours. Upon completion of the reaction, after cooling, the mixture was filtered and the filtrate was poured into 200 ml of ice-cold water. The precipitate thus formed was collected on a filter, washed with water, dried and crystallized from ethanol, to give 6.4 g of the title compound, melting at 226°-228° C.

Following the procedure described in the above Step 4, but starting from 0.92 g of the acid described in Step 3, and employing 0.3 g of bromoethanol and 0.276 g of anhydrous potassium carbonate instead of dicyclohexylcarbodiimide and the 4-N,N-dimethylaminopyridine, 0.33 g of methyl 2-hydroxyethyl 2,6-dimethyl-4-(3-methylflavon-8-yl)-1,4-dihydropyridine-3,5-dicarboxylate (ix) were obtained, melting at 201°-203° C.

In the same manner, but employing a suitable halogen-derivative instead of bromoethanol, the following compounds were prepared:

Methyl isopropyl 2,6-dimethyl-4-(3-methylflavon-8-yl)-1,4-dihydropyridine-3,5-dicarboxylate (x) (m.p. 209°-211° C.);

Methyl n-butyl 2,6-dimethyl-4-(3-methylflavon-8-yl)-1,4-dihydropyridine-3,5-dicarboxylate (xi) (m.p. 196°-198° C.);

Methyl propargyl 2,6-dimethyl-4-(3-methylflavon-8-yl)-1,4-dihydropyridine-3,5-dicarboxylate (xii) (m.p. 213°-216° C.);

Methyl allyl 2,6-dimethyl-4-(3-methylflavon-8yl)-1,4-dihydropyridine-3,5-dicarboxylate (xiii) (m.p. 219°-221° C.);

Methyl alpha-methylallyl 2,6-dimethyl-4-(3-methylflavon-8-yl)-1,4-dihydropyridine-3,5-dicarboxylate (xiv) (m.p. 187°-192° C.);

Methyl benzyl 2,6-dimethyl-4-(3-methylflavon-8-yl)-1,4-dihydropyridine-3,5-dicarboxylate (xv) (m.p. 204°-207° C.);

Methyl 2-oxopropyl 2,6-dimethyl-4-(3-methylflavon-8-yl)-1,4-dihydropyridine-3,5-dicarboxylate (xvi) (m.p. 182°-183° C.);

Methyl 2,3-dihydroxypropyl 2,6-dimethyl-4-(3-methylflavon-8-yl)-1,4-dihydropyridine-3,5-dicarboxylate (xvii) (m.p. 168°-170° C.);

Methyl 2-ethoxyethyl 2,6-dimethyl-4-(3-methylflavon-8-yl)-1,4-dihydropyridine-3,5-dicarboxylate (xviii) (m.p. 188°-191° C.);

Methyl 2-ethylthioethyl 2,6-dimethyl-4-(3-methylflavon-8-yl)-1,4-dihydropyridine-3,5-dicarboxylate (xix) (m.p. 165°-167° C.);

Methyl 2-acetoxyethyl 2,6-dimethyl-4-(3-methylflavon-8-yl)-1,4-dihydropyridine-3,5-dicarboxylate (xx) (m.p. 183°-186° C.);

Methyl 2-phenylethyl 2,6-dimethyl-4-(3-methylflavon-8-yl)-1,4-dihydropyridine-3,5-dicarboxylate (xxi) (m.p. 196°-199° C.);

Methyl 2-(N,N-dimethylamino)ethyl 2,6-dimethyl-4-(3-methylflavon-8-yl)-1,4-dihydropyridine-3,5-dicarboxylate (xxii) (m.p. 208°-210° C.).

EXAMPLE 4

Methyl 2-aminoethyl 2,6-dimethyl-4-(3-methylflavon-8-yl)-1,4-dihydropyridine-3,5-dicarboxylate (xxiii)

To a suspension of 5.34 g of the acid prepared as described in Step 3 of Example 3, in 24 ml of anhydrous methylene chloride and 6 ml of anhydrous dimethylformamide maintained under stirring and under a nitrogen atmosphere at −−5°/0° C., 1.64 g of thionyl chloride were added dropwise, over 5 minutes, and thereafter 1.35 g of 2-aminoethanol hydrochloride were added dropwise, over 30 minutes, at 0°/5° C. After standing for 3 hours at 20°-25° C., the mixture was cooled again on an ice-cold bath and 50 ml of 10% sodium carbonate were added dropwise. The organic phase was separated and washed with water (1×30 ml), with 25% acetic acid (V/V) and then with (2×60 ml) of water. The acidic and aqueous layers were combined, washed with ethyl ether (2×60 ml) and alkalinized with concentrated sodium hydroxide. After standing, the precipitate was collected, washed with water, dried and purified by silica-gel chromatography, eluting with a mixture of ethyl acetate/methanol/methanolic ammonia (about 7.5N) in a ratio of 92:8:4. 3.81 g of the title compound, melting at 188°-192° C., were obtained after crystallization from methylene chloride/ethyl ether.

Following the procedure described above, but employing a suitable alcohol instead of 2-aminoethanol, the following compounds were obtained:

Methyl 2-(N-methyl-N-phenylamino)ethyl 2,6-dimethyl-4-(3-methylflavon-8-yl)-1,4-dihydropyridine-3,5-dicarboxylate (xxiv) (m.p. 177°-182° C.);

Methyl 2-(N-methyl-N-cyclohexylamino)ethyl)2,6-dimethyl-4-(3-methylflavon-8-yl)-1,4-dihydropyridine-3,5-dicarboxylate (xxv) (m.p. 153°-155° C.);

Methyl 2,N-morpholinoethyl 2,6-dimethyl-4-(3-methylflavon-8-yl)-1,4-dihydropyridine-3,5-dicarboxylate (xxvi) (m.p. 215°-217° C.);

Methyl 2,N-imidazolylethyl 2,6-dimethyl-4-(3-methylflavon-8-yl)-1,4-dihydropyridine-3,5-dicarboxylate (xxvii) (m.p. 198°-200° C.);

Methyl 2,N-piperidinoethyl 2,6-dimethyl-4-(3-methylflavon-8-yl)-1,4-dihydropyridine-3,5-dicarboxylate (xxviii) (m.p. 189°-193° C.);

Methyl 2,N-piperidino-1,1-dimethylethyl 2,6-dimethyl-4-(3-methylflavon-8-yl)-1,4-dihydropyridine-3,5-dicarboxylate (xxix) (m.p. 212°-214° C.);

Methyl 2,N-methylaminoethyl 2,6-dimethyl-4-(3-methylflavon-8-yl)-1,4-dihydropyridine-3,5-dicarboxylate (xxx) (m.p. 180°-182° C.);

Methyl 2,N-(N′-methyl)piperazinoethyl 2,6-dimethyl-4-(3-methylflavon-8-yl)-1,4-dihydropyridine-3,5-dicarboxylate (xxxi) (m.p. 181°-185° C.);

Methyl tert-butyl 2,6-dimethyl-4-(3-methylflavon-8yl)-1,4-dihydropyridine-3,5-dicarboxylate (xxxii) (m.p. 222°-225° C.);

Methyl cyclohexyl 2,6-dimethyl-4-(3-methylflavon-8-yl)-1,4-dihydropyridine-3,5-dicarboxylate (xxxiii) (m.p. 137°-139° C.);

Methyl phenyl 2,6-dimethyl-4-(3-methylflavon-8-yl)-1,4-dihydropyridine-3,5-dicarboxylate (xxxiv) (m.p. 211°–213° C.);

Methyl 2-ethylsulfonylethyl 2,6-dimethyl-4-(3-methylflavon-8-yl)-1,4-dihydropyridine-3,5-dicarboxylate (xxxv) (m.p. 195°–200° C.).

EXAMPLE 5

Step 1

Preparation of methyl 4,4-dimethoxy-2-(3-methylflavon-8-methyliden)acetoacetate A mixture comprising 2.64 g of (II), 2.1 g of methyl 4,4-dimethoxyacetoacetate, 0.034 ml of acetic acid, 0.038 ml of piperidine and 8 ml of benzene, was heated to reflux under stirring for 12 hr, while the azeotropic mixture was distilled off. After cooling, the solution was first washed with 5% sodium bicarbonate, then with water, and dried over anhydrous sodium sulfate. After evaporation of the solvent, the residue was purified by silica-gel chromatography, eluting with petroleum ether/ethyl acetate first in a 4:1 ratio and then in a 3:2 ratio. The fractions containing the pure product were collected and the solvents were evaporated to give 2 g of the title compound that was used for the subsequent reaction without further purification.

A sample, crystallized from ethyl acetate adding petroleum ether, melted at 124°–126° C.

Step 2

Dimethyl 2-dimethoxymethyl-6-methyl-4-(3-methylflavon-8-yl)-1,4-dihydropyridine-3,5-dicarboxylate (xxxvi)

A mixture of 1.1 g of the acetoacetate described in the above step, 0.34 g of methyl 3-aminocrotonate and 1.5 ml of N,N-dimethylformamide, maintained under nitrogen atmosphere in the dark, was heated at 80° C. under stirring for 5 hr and then at 100°–105° C. for an additional 7 hr. After cooling, the mixture was diluted with about 15 ml of water and extracted with ethyl ester. The organic phase was washed with water, dried over sodium sulfate and, after evaporation of the solvent, the residue was purified by silica-gel chromatography, eluting with ethyl ether. The fractions containing the pure product were collected and, after evaporation of the solvent, the residue was crystallized from ethyl acetate adding petroleum ether, to give 0.32 g of the title compound, melting at 166°–168° C.

Step 3

Dimethyl 2-formyl-6-methyl-4-(3-methylflavon-8-yl)-1,4-dihydropyridine-3,5-dicarboxylate (xxxvii)

A solution of 10.15 g of the dimethoxymethyl derivative, obtained as described in the above Step 2, in 88 ml of acetone and 10 ml of 6N hydrochloric acid, was stirred under nitrogen atmosphere and in the dark for 5 hr at 18°–22° C. After dilution with 120 ml of water, 5.04 g of sodium bicarbonate were added portionwise and then most of the acetone was evaporated off, and the solids collected by filtration were purified by silica-gel chromatography, eluting with methylene chloride/ethyl ether (9:1). The fractions containing the pure compound were collected and, after evaporation of the solvent, the residue was crystallized from acetonitrile to give 4.6 g of the title compound, melting at 216° C.

EXAMPLE 6

Dimethyl 2-hydroxymethyl-6-methyl-4-(3-methylflavon-8-yl)-1,4-dihydropyridine-3,5-dicarboxylate (xxxviii)

To a mixture comprising 3.3 g of the 2-formyl derivative prepared as described in Step 3 of the previous Example, 52 ml of ethanol, 18 ml of methylene chloride, maintained under stirring at 0° C., under a nitrogen atmosphere and in the dark, 0.28 g of sodium borohydride was added portionwise. The solution was maintained under these conditions for 2 hr, then was acidified with 50% acetic acid, most of the solvents were evaporated under vacuum and to the residue were first added 70 ml of water and then 5% of sodium bicarbonate, until the reaction mixture was alkaline. The solids thus formed were collected by filtration and crystallized from acetonitrile to give 1.7 g of the title compound, melting at 231°–233° C.

EXAMPLE 7

Dimethyl 2-cyano-6-methyl-4-(3-methylflavon-8-yl)-1,4-dihydropyridine-3,5-dicarboxylate (xxxix)

A mixture comprising 0.95 g of the 2-formyl derivative prepared as described in the previous Example, 0.17 g of hydroxylamine hydrochloride, 0.245 g of anhydrous sodium acetate and 3.7 ml of acetic acid, was maintained under stirring at 18°–22° C. in the dark and under a nitrogen atmosphere for 4 hr. Thereafter, 0.75 g of acetic anhydride was added, and the mixture was adjusted to 18°–22° C. for 1 hr, and then heated to 95°–100° C. for 4 hr. After cooling, most of the acetic acid was evaporated under vacuum, and the residue was diluted with waer, neutralized with 5% sodium bicarbonate and then extracted with ethyl acetate. The crude material obtained after evaporation of the organic phase was purified by silica-gel chromatography, eluting with methylene chloride/ethyl acetate (9:1). The fractions containing the pure compound were collected, the solvents were evaporated and the residue crystallized from N,N-dimethylformamide/water to give 0.3 g of the title compound, melting at about 250° C.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A flavonyl-1,4-dihydropyridine having the formula:

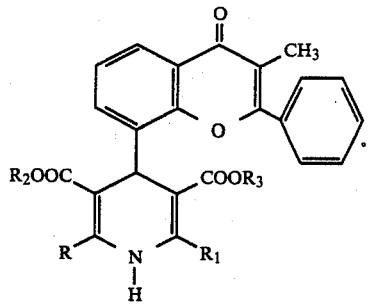

in which: R and $R_1$ are each independently selected from the group consisting of alkyl having from 1 to 4 carbon atoms, hydroxyalkyl having from 1 to 4 carbon atoms, formylalkyl and cyanoalkyl; and $R_2$ and $R_3$ are each independently selected from the group consisting of straight or branched chain alkyl having from 1 to 6 carbon atoms, straight or branched chain alkenyl having from 2 to 6 carbon atoms, alkynyl having from 2 to 6 carbon atoms, cycloalkyl having from 5 to 7 carbon atoms, phenylalkyl, phenyl, cyanoalkyl, haloalkyl, mono- or polyhydroxyalkyl, monoalkoxyalkyl, alkylthioalkyl, alkylsulfonylalkyl, monoalkanoyloxyalkyl, alkanoylalkyl, and $R_4R_5N$-straight or branched chain alkyl; wherein $R_4$ and $R_5$ are each independently selected from the group consisting of hydrogen, alkyl, cycloalkyl, phenylalkyl, phenyl, and 3,3-diphenylpropyl, or wherein $R_4$ and $R_5$ form together with their common nitrogen atom a 5- or 6-membered heterocycle optionally containing one other member selected from the group consisting of O, S, N and $NR_6$, in which $R_6$ is alkyl; or an optical isomer, a diasteromer or a pharmaceutically acceptable salt thereof.

2. The flavonyl-1,4-dihydropyridine as defined by claim 1, wherein at least one of R and $R_1$ is an alkyl radical having from 1 to 4 carbon atoms.

3. The flavonyl-1,4-dihydropyridine as defined by claim 1, wherein at least one of R and $R_1$ is an hydroxyalkyl radical having from 1 to 4 carbon atoms.

4. The flavonyl-1,4-dihydropyridine as defined by claim 1, wherein at least one of R and $R_1$ is a formyl(-lower alkyl) radical.

5. The flavonyl-1,4-dihydropyridine as defined by claim 1, wherein at least one of R and $R_1$ is a cyano(-lower alkyl) radical.

6. The flavonyl-1,4-dihydropyridine as defined by claim 1, wherein at least one of $R_2$ and $R_3$ is a straight or branched chain alkyl radical having from 1 to 6 carbon atoms.

7. The flavonyl-1,4-dihydropyridine as defined by claim 1, wherein at least one of $R_2$ and $R_3$ is a straight or branched chain alkenyl radical having from 2 to 6 carbon atoms.

8. The flavonyl-1,4-dihydropyridine as defined by claim 1, wherein at least one of $R_2$ and $R_3$ is an alkynyl radical having from 2 to 6 carbon atoms.

9. The flavonyl-1,4-dihydropyridine as defined by claim 1, wherein at least one of $R_2$ and $R_3$ is a cycloalkyl radical having from 5 to 7 carbon atoms.

10. The flavonyl-1,4-dihydropyridine as defined by claim 1, wherein at least one of $R_2$ and $R_3$ is an lower aralkyl radical.

11. The flavonyl-1,4-dihydropyridine as defined by claim 1, wherein at least one of $R_2$ and $R_3$ is a phenyl radical.

12. The flavonyl-1,4-dihydropyridine as defined by claim 1, wherein at least one of $R_2$ and $R_3$ is a cyano(-lower alkyl) radical.

13. The flavonyl-1,4-dihydropyridine as defined by claim 1, wherein at least one of $R_2$ and $R_3$ is a halo(-lower alkyl) radical.

14. The flavonyl-1,4-dihydropyridine as defined by claim 1, wherein at least one of $R_2$ and $R_3$ is a mono- or polyhydroxy(lower alkyl) radical.

15. The flavonyl-1,4-dihydropyridine as defined by claim 1, wherein at least one of $R_2$ and $R_3$ is a monohydroxy(lower alkyl) radical.

16. The flavonyl-1,4-dihydropyridine as defined by claim 1, wherein at least one of $R_2$ and $R_3$ is a lower alkylthio(lower alkyl) radical.

17. The flavonyl-1,4-dihydropyridine as defined by claim 1, wherein at least one of $R_2$ and $R_3$ is a lower alkylsulfonyl(lower alkyl) radical.

18. The flavonyl-1,4-dihydropyridine as defined by claim 1, wherein at least one of $R_2$ and $R_3$ is a mono(-lower acyl)oxy(lower alkyl) radical.

19. The flavonyl-1,4-dihydropyridine as defined by claim 1, wherein at least one of $R_2$ and $R_3$ is a lower acyl(lower alkyl) radical.

20. The flavonyl-1,4-dihydropyridine as defined by claim 1, wherein at least one of $R_2$ and $R_3$ is an $R_4R_5$N-alkyl radical, the alkyl moiety of which being straight or branched chain and having from 2 to 6 carbon atoms, and in which $R_4$ and $R_5$, which may be identical or different, are each hydrogen, or a lower alkyl, lower cycloalkyl, lower alkyl, phenyl or 3,3-diphenylpropyl radical, with the proviso that $R_4$ and $R_5$ may together form, with the nitrogen atom from which they depend, a saturated or unsaturated heterocycle having from 4 to 7 ring members, and optionally containing one or more other O, S or N heteroatoms, or a group $NR_6$, in which $R_6$ is a lower alkyl radical.

21. The flavonyl-1,4-dihydropyridine as defined by claim 1, the same being dimethyl 2,6-dimethyl-4-(3-methylflavon-8-yl)-1,4-dihydropyridine-3,5-dicarboxylate.

22. The flavonyl-1,4-dihydropyridine as defined by claim 1, the same being bis-2,N-piperidinoethyl 2,6-dimethyl-4-(3-methylflavon-8-yl)-1,4-dihydropyridine-3,5-dicarboxylate.

23. The flavonyl-1,4-dihydropyridine as defined by claim 1, the same being isopropyl beta-chloroethyl 2,6-dimethyl-4-(3-methylflavon-8-yl)-1,4-dihydropyridine-3,5-dicarboxylate.

24. The flavonyl-1,4-dihydropyridine as defined by claim 1, the same being isopropyl 2,N-piperidinoethyl 2,6-dimethyl-4-(3-methylflavon-8-yl)-1,4-dihydropyridine-3,5-dicarboxylate.

25. The flavonyl-1,4-dihydropyridine as defined by claim 1, the same being isopropyl 2-(N-benzyl-N-methylamino)ethyl 2,6-dimethyl-4-(3-methylflavon-8-yl)-1,4-dihydropyridine-3,5-dicarboxylate.

26. The flavonyl-1,4-dihydropyridine as defined by claim 1, the same being isopropyl 2-(N-(3,3-diphenylpropyl)-N-methylamino)ethyl 2,6-dimethyl-4-(3-methylflavon-8-yl)-1,4-dihydropyridine-3,5-dicarboxylate.

27. The flavonyl-1,4-dihydropyridine as defined by claim 1, the same being methyl 2-cyanoethyl 2,6-dimethyl-4-(3-methylflavon-8-yl)-1,4-dihydropyridine-3,5-dicarboxylate.

28. The flavonyl-1,4-dihydropyridine as defined by claim 1, the same being methyl ethyl 2,6-dimethyl-4-(3- methylflavon-8-yl)-1,4-dihydropyridine-3,5-dicarboxylate.

29. The flavonyl-1,4-dihydropyridine as defined by claim 1, the same being methyl 2-hydroxyethyl 2,6-dimethyl-4-(3-methylflavon-8-yl)-1,4-dihydropyridine-3,5-dicarboxylate.

30. The flavonyl-1,4-dihydropyridine as defined by claim 1, the same being methyl isopropyl 2,6-dimethyl-4-(3-methylflavon-8-yl)-1,4-dihydropyridine-3,5-dicarboxylate.

31. The flavonyl-1,4-dihydropyridine as defined by claim 1, the same being methyl n-butyl 2,6-dimethyl-4-(3-methylflavon-8-yl)-1,4-dihydropyridine-3,5-dicarboxylate.

32. The flavonyl-1,4-dihydropyridine as defined by claim 1, the same being methyl propargyl 2,6-dimethyl-4-(3-methylflavon-8-yl)-1,4-dihydropyridine-3,5-dicarboxylate.

33. The flavonyl-1,4-dihydropyridine as defined by claim 1, the same being methyl allyl 2,6-dimethyl-4-(3-methylflavon-8-yl)-1,4-dihydropyridine-3,5-dicarboxylate.

34. The flavonyl-1,4-dihydropyridine as defined by claim 1, the same being methyl alpha-methylallyl 2,6-dimethyl-4-(3-methylflavon-8-yl)-1,4-dihydropyridine-3,5-dicarboxylate.

35. The flavonyl-1,4-dihydropyridine as defined by claim 1, the same being methyl benzyl 2,6-dimethyl-4-(3-methylflavon-8-yl)-1,4-dihydropyridine-3,5-dicarboxylate.

36. The flavonyl-1,4-dihydropyridine as defined by claim 1, the same being methyl 2-oxopropyl 2,6-dimethyl-4-(3-methylflavon-8-yl)-1,4-dihydropyridine-3,5-dicarboxylate.

37. The flavonyl-1,4-dihydropyridine as defined by claim 1, the same being methyl 2,3-dihydroxypropyl 2,6-dimethyl-4-(3-methylflavon-8-yl)-1,4-dihydropyridine-3,5-dicarboxylate.

38. The flavonyl-1,4-dihydropyridine as defined by claim 1, the same being methyl 2-ethoxyethyl 2,6-dimethyl-4-(3-methylflavon-8-yl)-1,4-dihydropyridine-3,5-dicarboxylate.

39. The flavonyl-1,4-dihydropyridine as defined by claim 1, the same being methyl 2-ethylthioethyl 2,6-dimethyl-4-(3-methylflavon-8-yl)-1,4-dihydropyridine-3,5-dicarboxylate.

40. The flavonyl-1,4-dihydropyridine as defined by claim 1, the same being methyl 2-acetoxyethyl 2,6-dimethyl-4-(3-methylflavon-8-yl)-1,4-dihydropyridine-3,5-dicarboxylate.

41. The flavonyl-1,4-dihydropyridine as defined by claim 1, the same being methyl 2-phenylethyl 2,6-dimethyl-4-(3-methylflavon-8-yl)-1,4-dihydropyridine-3,5-dicarboxylate.

42. The flavonyl-1,4-dihydropyridine as defined by claim 1, the same being methyl 2-(N,N-dimethylamino)ethyl 2,6-dimethyl-4-(3-methylflavon-8-yl)-1,4-dihydropyridine-3,5-dicarboxylate.

43. The flavonyl-1,4-dihydropyridine as defined by claim 1, the same being methyl 2-aminoethyl 2,6-dimethyl-4-(3-methylflavon-8-yl)-1,4-dihydropyridine-3,5-dicarboxylate.

44. The flavonyl-1,4-dihydropyridine as defined by claim 1, the same being methyl 2-(N-methyl-N-phenylamino)ethyl 2,6-dimethyl-4-(3-methylflavon-8-yl)-1,4-dihydropyridine-3,5-dicarboxylate.

45. The flavonyl-1,4-dihydropyridine as defined by claim 1, the same being methyl 2-(N-methyl-N-cyclohexylamino)ethyl 2,6-dimethyl-4-(3-methylflavon-8-yl)-1,4-dihydropyridine-3,5-dicarboxylate.

46. The flavonyl-1,4-dihydropyridine as defined by claim 1, the same being methyl 2,N-morpholinoethyl 2,6-dimethyl-4-(3-methylflavon-8-yl)-1,4-dihydropyridine-3,5-dicarboxylate.

47. The flavonyl-1,4-dihydropyridine as defined by claim 1, the same being methyl 2,N-imidazolylethyl 2,6-dimethyl-4-(3-methylflavon-8-yl)-1,4-dihydropyridine-3,5-dicarboxylate.

48. The flavonyl-1,4-dihydropyridine as defined by claim 1, the same being methyl 2,N-piperidinoethyl 2,6-dimethyl-4-(3-methylflavon-8-yl)-1,4-dihydropyridine 3,5-dicarboxylate.

49. The flavonyl-1,4-dihydropyridine as defined by claim 1, the same being methyl 2,N-piperidino-1,1-dimethylethyl 2,6-dimethyl-4-(3-methylflavon-8-yl)-1,4-dihydropyridine-3,5-dicarboxylate.

50. The flavonyl-1,4-dihydropyridine as defined by claim 1, the same being methyl 2,N-methylaminoethyl 2,6-dimethyl-4-(3-methylflavon-8-yl)-1,4-dihydropyridine-3,5-dicarboxylate.

51. The flavonyl-1,4-dihydropyridine as defined by claim 1, the same being methyl 2,N-(N'-methyl)-piperazinoethyl 2,6-dimethyl-4-(3-methylflavon-8-yl)-1,4-dihydropyridine-3,5-dicarboxylate.

52. The flavonyl-1,4-dihydropyridine as defined by claim 1, the same being methyl tert-butyl 2,6-dimethyl-4-(3-methylflavon-8-yl)-1,4-dihydropyridine-3,5-dicarboxylate.

53. The flavonyl-1,4-dihydropyridine as defined by claim 1, the same being methyl cyclohexyl 2,6-dimethyl-4-(3-methylflavon-8-yl)-1,4-dihydropyridine-3,5-dicarboxylate.

54. The flavonyl-1,4-dihydropyridine as defined by claim 1, the same being methyl phenyl 2,6-dimethyl-4-(3-methylflavon-8-yl)-1,4-dihydropyridine-3,5-dicarboxylate.

55. The flavonyl-1,4-dihydropyridine as defined by claim 1, the same being methyl 2-ethylsulfonylethyl 2,6-dimethyl-4-(3-methylflavon-8-yl)-1,4-dihydropyridine-3,5-dicarboxylate.

56. The flavonyl-1,4-dihydropyridine as defined by claim 1, the same being dimethyl 2-formyl-6-methyl-4-(3-methylflavon-8-yl)-1,4-dihydropyridine-3,5-dicarboxylate.

57. The flavonyl-1,4-dihydropyridine as defined by claim 1, the same being dimethyl 2-hydroxymethyl-6-methyl-4-(3-methylflavon-8-yl)-1,4-dihydropyridine-3,5-dicarboxylate.

58. The flavonyl-1,4-dihydropyridine as defined by claim 1, the same being dimethyl 2-cyano-6-methyl-4-(3-methylflavon-8-yl)-1,4-dihydropyridine-3,5-dicarboxylate.

59. A composition of matter for eliciting a calcium-antagonistic or smooth muscle relaxant response in a mammalian organism in need of such treatment, comprising a therapeutically effective amount of the flavonyl-1,4-dihydropyridine as defined by claim 1, and a pharmaceutically acceptable carrier therefor.

60. A method of eliciting a calcium-antagonistic or smooth muscle relaxant response in a mammalian organism in need of such treatment, comprising administering to such organism a therapeutically effective amount of the flavonyl-1,4-dihydropyridine as defined by claim 1.

61. A method of eliciting a calcium-antagonistic or smooth muscle relaxant response in a mammalian organism in need of such treatment, comprising administering to such organism the composition of matter as defined by claim 59.

* * * * *